US008092504B2

(12) United States Patent
Warnick (10) Patent No.: US 8,092,504 B2
(45) Date of Patent: *Jan. 10, 2012

(54) PEDICLE SCREW SYSTEMS AND METHODS OF ASSEMBLING/INSTALLING THE SAME

(75) Inventor: David R. Warnick, Spanish Fork, UT (US)

(73) Assignee: X-spine Systems, Inc., Miamisburg, OH (US)

(*) Notice: Subject to any disclaimer, the term of this patent is extended or adjusted under 35 U.S.C. 154(b) by 169 days.

This patent is subject to a terminal disclaimer.

(21) Appl. No.: 11/942,443

(22) Filed: Nov. 19, 2007

(65) Prior Publication Data
US 2008/0071277 A1 Mar. 20, 2008

Related U.S. Application Data

(63) Continuation of application No. 11/258,831, filed on Oct. 25, 2005, now Pat. No. 7,662,172.

(60) Provisional application No. 60/622,107, filed on Oct. 25, 2004, provisional application No. 60/622,180, filed on Oct. 25, 2004, provisional application No. 60/629,785, filed on Nov. 19, 2004, provisional application No. 60/663,092, filed on Mar. 18, 2005, provisional application No. 60/684,697, filed on May 25, 2005.

(51) Int. Cl.
*A61B 17/70* (2006.01)

(52) U.S. Cl. ......... 606/269; 606/266; 606/267; 606/265

(58) Field of Classification Search .......... 606/250–279, 606/300–320, 246–249; 403/341, 349
See application file for complete search history.

(56) References Cited

U.S. PATENT DOCUMENTS

| 483,342 A | 9/1892 | Bolte |
| 900,717 A | 10/1908 | Feaster |
| 920,188 A | 5/1909 | Schumacher |
| 1,171,380 A * | 2/1916 | Arthur ..................... 285/349 |

(Continued)

FOREIGN PATENT DOCUMENTS

DE 3219575 A1 12/1983

(Continued)

OTHER PUBLICATIONS

Expedium Spine System, DePuy Spine, Raynham, MA 02767.

*Primary Examiner* — Eduardo C Robert
*Assistant Examiner* — Jan Christopher Merene
(74) *Attorney, Agent, or Firm* — Jacox, Meckstroth & Jenkins (57) ABSTRACT

The pedicle screw system may be used for fixation of spinal segments and may be advantageous when minimally invasive surgery (MIS) techniques are employed. The pedicle screw system includes a tulip assembly comprising of a tulip body, a inner member, and an expansion member.

Installation of the pedicle screw system into pedicles of the spine, for example, includes inserting the pedicle screw into a portion of the spine and then coupling the tulip assembly to the pedicle screw. The tulip assembly may be locked onto the pedicle screw before a distraction rod is placed in the tulip assembly. After the rod is placed in the tulip assembly, the tulip body and the inner member can be rotated relative to one another to lock the rod into the tulip assembly. In addition, the relative rotation may also provide additional locking of the tulip assembly to the pedicle screw.

12 Claims, 7 Drawing Sheets

U.S. PATENT DOCUMENTS

| | | | |
|---|---|---|---|
| 1,536,559 A | 5/1925 | Carroll | |
| 2,344,381 A | 3/1944 | Young | |
| 3,019,504 A | 2/1962 | Castagliuolo | |
| 3,648,691 A | 3/1972 | Lumb et al. | |
| 3,752,203 A | 8/1973 | Hill, Jr. | |
| 3,851,601 A * | 12/1974 | Davis | 108/158.11 |
| 3,875,936 A | 4/1975 | Volz | |
| 4,011,602 A | 3/1977 | Rybicki et al. | |
| 4,085,744 A | 4/1978 | Lewis et al. | |
| 4,269,178 A | 5/1981 | Keene | |
| 4,289,124 A | 9/1981 | Zickel | |
| 4,294,300 A | 10/1981 | Bouwman | |
| 4,309,139 A | 1/1982 | Nakae | |
| 4,411,259 A | 10/1983 | Drummond | |
| 4,604,995 A | 8/1986 | Stephens et al. | |
| 4,611,580 A | 9/1986 | Wu | |
| 4,611,581 A | 9/1986 | Steffee | |
| 4,641,636 A | 2/1987 | Cotrel | |
| 4,648,388 A | 3/1987 | Steffee | |
| 4,653,481 A | 3/1987 | Howland et al. | |
| 4,655,199 A | 4/1987 | Steffee | |
| 4,658,809 A | 4/1987 | Ulrich et al. | |
| 4,696,290 A | 9/1987 | Steffee | |
| 4,719,905 A | 1/1988 | Steffee | |
| 4,763,644 A | 8/1988 | Webb | |
| 4,771,767 A | 9/1988 | Steffee | |
| 4,805,602 A | 2/1989 | Puno et al. | |
| 4,815,453 A | 3/1989 | Cotrel | |
| 4,887,595 A | 12/1989 | Heinig et al. | |
| 4,887,596 A | 12/1989 | Sherman | |
| 4,913,134 A | 4/1990 | Luque | |
| 4,946,458 A | 8/1990 | Harms et al. | |
| 4,950,269 A | 8/1990 | Gaines | |
| 5,005,562 A | 4/1991 | Cotrel | |
| 5,024,213 A | 6/1991 | Asher et al. | |
| 5,042,982 A | 8/1991 | Harms et al. | |
| 5,067,955 A | 11/1991 | Cotrel | |
| 5,084,049 A | 1/1992 | Asher et al. | |
| 5,092,867 A | 3/1992 | Harms et al. | |
| 5,113,685 A | 5/1992 | Asher et al. | |
| 5,120,171 A | 6/1992 | Lasner | |
| 5,127,912 A | 7/1992 | Ray et al. | |
| 5,129,900 A | 7/1992 | Asher et al. | |
| 5,154,719 A | 10/1992 | Cotrel | |
| 5,176,680 A | 1/1993 | Vignaud et al. | |
| 5,183,359 A | 2/1993 | Barth | |
| 5,190,543 A | 3/1993 | Schlapfer | |
| 5,196,013 A | 3/1993 | Harms et al. | |
| 5,207,678 A | 5/1993 | Harms et al. | |
| 5,246,303 A * | 9/1993 | Trilla et al. | 403/353 |
| 5,257,993 A | 11/1993 | Asher et al. | |
| 5,261,913 A | 11/1993 | Marnay | |
| 5,312,402 A | 5/1994 | Schlapfer | |
| 5,346,493 A | 9/1994 | Stahurski et al. | |
| 5,360,431 A | 11/1994 | Puno et al. | |
| 5,380,325 A | 1/1995 | Lahille et al. | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,520,689 A | 5/1996 | Schlapfer | |
| 5,534,001 A * | 7/1996 | Schlapfer et al. | 606/302 |
| 5,549,608 A | 8/1996 | Errico et al. | |
| 5,562,663 A | 10/1996 | Wisnewski et al. | |
| 5,603,714 A | 2/1997 | Kaneda et al. | |
| 5,609,593 A | 3/1997 | Errico et al. | |
| 5,624,442 A | 4/1997 | Mellinger et al. | |
| 5,647,873 A | 7/1997 | Errico et al. | |
| 5,667,508 A | 9/1997 | Errico et al. | |
| 5,669,911 A | 9/1997 | Errico et al. | |
| 5,690,630 A | 11/1997 | Errico et al. | |
| 5,733,285 A | 3/1998 | Errico et al. | |
| 5,797,911 A | 8/1998 | Sherman et al. | |
| 5,817,094 A | 10/1998 | Errico et al. | |
| 5,879,350 A | 3/1999 | Sherman | |
| 5,882,350 A | 3/1999 | Ralph | |
| 5,885,286 A | 3/1999 | Sherman et al. | |
| 5,891,145 A | 4/1999 | Morrison et al. | |
| 5,954,725 A | 9/1999 | Sherman | |
| 6,010,503 A | 1/2000 | Richelsoph | |
| 6,063,090 A | 5/2000 | Schlapfer | |
| 6,077,262 A | 6/2000 | Schlapfer et al. | |
| 6,090,111 A | 7/2000 | Nichols | |
| 6,113,601 A | 9/2000 | Tatar | |
| 6,132,432 A | 10/2000 | Richelsoph | |
| 6,235,033 B1 | 5/2001 | Brace et al. | |
| 6,280,442 B1 | 8/2001 | Barker et al. | |
| 6,302,888 B1 | 10/2001 | Mellinger et al. | |
| RE37,665 E | 4/2002 | Ralph | |
| 6,371,957 B1 | 4/2002 | Amrein et al. | |
| 6,402,752 B2 | 6/2002 | Schaffler-Wachter | |
| 6,451,021 B1 | 9/2002 | Ralph | |
| 6,475,218 B2 | 11/2002 | Gournay et al. | |
| 6,488,681 B2 | 12/2002 | Martin et al. | |
| 6,623,485 B2 | 9/2003 | Doubler et al. | |
| 6,626,908 B2 | 9/2003 | Cooper et al. | |
| 6,652,526 B1 | 11/2003 | Arafiles | |
| 6,660,004 B2 | 12/2003 | Barker et al. | |
| 6,716,214 B1 | 4/2004 | Jackson | |
| 6,730,089 B2 | 5/2004 | Jackson | |
| 6,730,093 B2 | 5/2004 | Saint Martin | |
| 6,755,829 B1 | 6/2004 | Bono et al. | |
| 6,786,903 B2 | 9/2004 | Lin | |
| 6,793,657 B2 | 9/2004 | Lee et al. | |
| 6,802,844 B2 | 10/2004 | Ferree | |
| 6,827,719 B2 | 12/2004 | Ralph | |
| 6,840,940 B2 | 1/2005 | Ralph | |
| 6,843,791 B2 | 1/2005 | Serhan | |
| 6,858,030 B2 | 2/2005 | Martin et al. | |
| 6,863,464 B1 * | 3/2005 | Niklaus | 403/341 |
| 6,869,433 B2 | 3/2005 | Glascott | |
| 6,896,677 B1 | 5/2005 | Lin | |
| 7,022,122 B2 | 4/2006 | Amrein | |
| 7,081,117 B2 | 7/2006 | Bono et al. | |
| 7,083,621 B2 | 8/2006 | Shaolian et al. | |
| 7,125,426 B2 | 10/2006 | Moumene et al. | |
| 7,141,051 B2 | 11/2006 | Janowski et al. | |
| 7,261,715 B2 | 8/2007 | Rezach et al. | |
| 7,291,151 B2 | 11/2007 | Alvarez | |
| 7,291,153 B2 | 11/2007 | Glascott | |
| 7,294,128 B2 | 11/2007 | Alleyne et al. | |
| 7,322,981 B2 | 1/2008 | Jackson | |
| 7,338,491 B2 | 3/2008 | Baker et al. | |
| 7,377,923 B2 | 5/2008 | Purcell et al. | |
| 7,524,325 B2 | 4/2009 | Khalili | |
| 7,657,960 B2 * | 2/2010 | Umbrell | 15/230.19 |
| 7,682,377 B2 | 3/2010 | Konieczynski et al. | |
| 2002/0013585 A1 | 1/2002 | Gournay et al. | |
| 2002/0026193 A1 | 2/2002 | Barker et al. | |
| 2002/0082601 A1 | 6/2002 | Toyama et al. | |
| 2002/0091386 A1 | 7/2002 | Martin et al. | |
| 2002/0111626 A1 | 8/2002 | Ralph et al. | |
| 2002/0120272 A1 | 8/2002 | Yuan et al. | |
| 2002/0133154 A1 | 9/2002 | Saint Martin | |
| 2002/0133158 A1 | 9/2002 | Saint Martin | |
| 2002/0143341 A1 | 10/2002 | Biedermann | |
| 2002/0151900 A1 | 10/2002 | Glascott | |
| 2002/0183748 A1 | 12/2002 | Martin et al. | |
| 2003/0032957 A1 * | 2/2003 | McKinley | 606/61 |
| 2003/0073996 A1 | 4/2003 | Doubler et al. | |
| 2003/0078583 A1 | 4/2003 | Biedermann et al. | |
| 2003/0187433 A1 | 10/2003 | Lin | |
| 2003/0187434 A1 | 10/2003 | Lin | |
| 2003/0199873 A1 | 10/2003 | Richelsoph | |
| 2003/0231927 A1 * | 12/2003 | Hale | 403/349 |
| 2004/0039383 A1 | 2/2004 | Jackson | |
| 2004/0039384 A1 | 2/2004 | Boehm | |
| 2004/0049190 A1 | 3/2004 | Biedermann | |
| 2004/0097933 A1 | 5/2004 | Lourdel et al. | |
| 2004/0116929 A1 | 6/2004 | Barker et al. | |
| 2004/0127896 A1 | 7/2004 | Lombardo et al. | |
| 2004/0138662 A1 | 7/2004 | Landry et al. | |
| 2004/0153068 A1 | 8/2004 | Janowski et al. | |
| 2004/0172020 A1 | 9/2004 | Beaurain et al. | |
| 2004/0172022 A1 | 9/2004 | Landry et al. | |
| 2004/0236330 A1 | 11/2004 | Purcell et al. | |
| 2004/0249380 A1 | 12/2004 | Glascott | |
| 2004/0267264 A1 | 12/2004 | Konieczynski et al. | |

| | | |
|---|---|---|
| 2005/0033296 A1 | 2/2005 | Bono et al. |
| 2005/0049589 A1 | 3/2005 | Jackson |
| 2005/0096653 A1* | 5/2005 | Doubler et al. .................. 606/61 |
| 2005/0113830 A1 | 5/2005 | Rezach et al. |
| 2005/0131410 A1 | 6/2005 | Lin |
| 2005/0177154 A1 | 8/2005 | Moumene et al. |
| 2005/0177157 A1 | 8/2005 | Jahng |
| 2005/0182400 A1 | 8/2005 | White |
| 2005/0187548 A1 | 8/2005 | Butler et al. |
| 2005/0192570 A1 | 9/2005 | Jackson |
| 2005/0192571 A1 | 9/2005 | Abdelgany |
| 2005/0192573 A1 | 9/2005 | Abdelgany |
| 2005/0203515 A1 | 9/2005 | Doherty et al. |
| 2005/0203516 A1 | 9/2005 | Biedermann et al. |
| 2005/0203519 A1 | 9/2005 | Harms et al. |
| 2005/0215998 A1 | 9/2005 | Donath |
| 2005/0215999 A1 | 9/2005 | Birkmeyer et al. |
| 2005/0216003 A1 | 9/2005 | Biedermann et al. |
| 2005/0216004 A1 | 9/2005 | Schwab |
| 2005/0222570 A1 | 10/2005 | Jackson |
| 2005/0240180 A1 | 10/2005 | Vienney et al. |
| 2005/0261687 A1 | 11/2005 | Garamszegi et al. |
| 2006/0025767 A1 | 2/2006 | Khalili |
| 2006/0025771 A1 | 2/2006 | Jackson |
| 2006/0069391 A1 | 3/2006 | Jackson |
| 2006/0084982 A1 | 4/2006 | Kim |
| 2006/0084984 A1 | 4/2006 | Kim |
| 2006/0084987 A1 | 4/2006 | Kim |
| 2006/0089644 A1 | 4/2006 | Felix |
| 2006/0100621 A1 | 5/2006 | Jackson |
| 2006/0100622 A1 | 5/2006 | Jackson |
| 2006/0111712 A1 | 5/2006 | Jackson |
| 2006/0111715 A1 | 5/2006 | Jackson |
| 2006/0129147 A1 | 6/2006 | Biedermann et al. |
| 2006/0129149 A1 | 6/2006 | Iott et al. |
| 2006/0155278 A1 | 7/2006 | Warnick |
| 2006/0161152 A1 | 7/2006 | Ensign et al. |
| 2006/0161153 A1 | 7/2006 | Hawkes et al. |
| 2006/0173456 A1 | 8/2006 | Hawkes et al. |
| 2006/0195086 A1 | 8/2006 | Sybert |
| 2006/0200128 A1 | 9/2006 | Mueller |
| 2006/0217716 A1 | 9/2006 | Baker et al. |
| 2006/0229615 A1 | 10/2006 | Abdou |
| 2006/0235392 A1 | 10/2006 | Hammer et al. |
| 2006/0235393 A1 | 10/2006 | Bono et al. |
| 2006/0241603 A1 | 10/2006 | Jackson |
| 2006/0264933 A1 | 11/2006 | Baker et al. |
| 2006/0276792 A1 | 12/2006 | Ensign et al. |
| 2006/0293659 A1 | 12/2006 | Alvarez |
| 2006/0293664 A1 | 12/2006 | Schumacher |
| 2007/0043357 A1 | 2/2007 | Kirschman |
| 2007/0043359 A1 | 2/2007 | Altarac et al. |
| 2007/0053765 A1 | 3/2007 | Warnick et al. |
| 2007/0055242 A1 | 3/2007 | Bailly |
| 2007/0090238 A1 | 4/2007 | Justis |
| 2007/0093817 A1 | 4/2007 | Barrus et al. |
| 2007/0093821 A1 | 4/2007 | Freudiger |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0093832 A1 | 4/2007 | Abdelgany |
| 2007/0100341 A1 | 5/2007 | Reglos et al. |
| 2007/0123862 A1 | 5/2007 | Warnick |
| 2007/0123867 A1 | 5/2007 | Kirschman |
| 2007/0162008 A1 | 7/2007 | Cline, Jr. et al. |
| 2007/0167949 A1 | 7/2007 | Altarac et al. |
| 2007/0173819 A1 | 7/2007 | Sandlin |
| 2007/0239159 A1 | 10/2007 | Altarac et al. |
| 2007/0288004 A1 | 12/2007 | Alvarez |
| 2007/0293861 A1 | 12/2007 | Rezach et al. |
| 2008/0004625 A1 | 1/2008 | Runco et al. |
| 2008/0039839 A1 | 2/2008 | Songer et al. |
| 2008/0039840 A1 | 2/2008 | Songer et al. |
| 2008/0045953 A1 | 2/2008 | Garamszegi |
| 2008/0045956 A1 | 2/2008 | Songer et al. |
| 2008/0086131 A1 | 4/2008 | Daly et al. |
| 2008/0097441 A1 | 4/2008 | Hayes et al. |
| 2008/0097457 A1 | 4/2008 | Warnick |
| 2008/0167689 A1 | 7/2008 | Matthis et al. |
| 2008/0249576 A1 | 10/2008 | Hawkes et al. |
| 2010/0004693 A1* | 1/2010 | Miller et al. .................. 606/308 |

FOREIGN PATENT DOCUMENTS

| | | |
|---|---|---|
| DE | 3639810 A1 | 5/1988 |
| DE | 3711013 C1 | 6/1988 |
| DE | 9403231 U1 | 4/1994 |
| EP | 128058 A1 | 12/1984 |
| EP | 242705 A2 | 10/1987 |
| EP | 242708 A2 | 10/1987 |
| EP | 1190678 A2 | 3/2002 |
| EP | 1210914 A1 | 5/2002 |
| EP | 1604617 A1 | 12/2005 |
| FR | 2615095 A1 | 11/1988 |
| FR | 2624720 A1 | 6/1989 |
| FR | 2706762 A1 | 12/1994 |
| FR | 2852815 A1 | 10/2004 |
| GB | 167228 A | 7/1921 |
| GB | 2173104 A | 10/1986 |
| WO | 8707134 A1 | 12/1987 |
| WO | WO 00/36308 A1 * | 6/2000 |
| WO | 0152758 A1 | 6/2001 |
| WO | 02080788 A1 | 10/2002 |
| WO | 03086204 A2 | 4/2003 |
| WO | 2004103194 A1 | 5/2004 |
| WO | 2004089245 A2 | 10/2004 |
| WO | 2006047555 A2 | 5/2006 |
| WO | 2006047707 A2 | 5/2006 |
| WO | 2006047711 A2 | 5/2006 |
| WO | 2007075454 A1 | 7/2007 |
| WO | 2008008511 A2 | 1/2008 |

* cited by examiner

PEDICLE SCREW SYSTEMS AND METHODS OF ASSEMBLING/INSTALLING THE SAME

CROSS-REFERENCES TO RELATED APPLICATIONS

This application is a Continuation Application of U.S. application Ser. No. 11/258,831, filed Oct. 25, 2005, which is now U.S. Pat. No. 7,662,172, which application claims the benefit under 35 U.S.C. sctn. 119(e) of U.S. Provisional Patent Application Nos. 60/622,107 filed Oct. 25, 2004; 60/622,180 filed Oct. 25, 2004; 60/629,785 filed Nov. 19, 2004; 60/663,092 filed Mar. 18, 2005; and 60/684,697 filed May 25, 2005, which applications are incorporated herein by reference in their entireties.

BACKGROUND OF THE INVENTION

1. Field of the Invention

The present invention relates generally to bone fixation devices, and in particular to a screw assembly for the internal fixation of vertebral bodies.

2. Description of the Related Art

Various devices for internal fixation of bone segments in the human or animal body are known in the art. One type of system is a pedicle screw system, which is sometimes used as an adjunct to spinal fusion surgery, and which provides a means of gripping a spinal segment. A conventional pedicle screw system comprises a pedicle screw and a rod-receiving device. The pedicle screw includes an externally threaded stem and a head portion. The rod-receiving device couples to the head portion of the pedicle screw and receives a rod (commonly referred to as a distraction rod). Two such systems are inserted into respective vertebrae and adjusted to distract and/or stabilize a spinal column, for instance during an operation to correct a herniated disk. The pedicle screw does not, by itself, fixate the spinal segment, but instead operates as an anchor point to receive the rod-receiving device, which in turn receives the rod. One goal of such a system is to substantially reduce and/or prevent relative motion between the spinal segments that are being fused.

Although conventional prior art pedicle screw systems exist, they lack features that enhance and/or benefit newer, minimally invasive surgery (MIS) techniques that are more commonly being used for spinal surgeries. It has been suggested that one possible advantage of an MIS approach is that it can decrease a patient's recovery time. Conventional pedicle screw systems and even more recently designed pedicle screw systems have several drawbacks. Some of these pedicle screw systems are rather large and bulky, which may result in more tissue damage in and around the surgical site when the pedicle screw system is installed during surgery. The prior art pedicle screw systems have a rod-receiving device that is pre-operatively coupled or attached to the pedicle screw. In addition, some of the prior art pedicle screw systems include numerous components that must all be carefully assembled together. For example, one type of pedicle screw system that may require up to nine (9) different components is disclosed in U.S. Published Patent Application Nos. 2005/0203516 and 2005/0216003 to Biedermann et al. One drawback that is common among many prior art pedicle screw systems is that a threaded component is used to lock down the rod in the rod-receiving device. Examples of these types of systems can be found in U.S. Published Patent Application Nos. 2005/0192571 to Abdelgany; 2005/019:2573 to Abdelgany et al.; the Biedermann et al. applications; 2005/0187548 to Butler et al.; 2005/0203515 to Doherty et al.; and 2004/0172022 to Landry et al. Each of these pedicle screw systems have an externally threaded fastening element either directly or indirectly coupled to the vertically extending walls of the rod-receiving device (e.g., referred to as a bone fixator, a receiving part, a coupling construct, etc.).

One problem associated with the above-identified pedicle screw systems is that cross-threading may occur when the fastening element is installed. Cross-threading may cause the fastening element to jam and/or may result in an improper construct where some components may not be in the correct position. Due to the dynamic nature of spinal movement, a cross-threaded pedicle screw system may be more prone to post-operative failure.

Another problem with the above-identified pedicle screw systems is that the coupling between the fastening element and the rod-receiving device when subjected to dynamic, post-operative loading may result in the walls of the rod-receiving device splaying apart. In the above-identified pedicle screw systems, the walls of the rod-receiving device are unsupported. Post-operative tulip splaying, as it is commonly called, may result in the dislodgment of the fastening element and the rod. In short, the pedicle screw system may become post-operatively disassembled and no longer function according to its intended purpose.

Other prior art pedicle screw systems have attempted to address some of the aforementioned drawbacks. For example, U.S. Pat. Nos. 5,609,593, 5,647,873, 5,667,508, 5,669,911, and 5,690,630, all to Errico et al., disclose a threaded, outer cap that extends over and couples to the walls of the rod-receiving device. However, the risk and/or potential for cross-threading is still present when the threaded, outer cap is coupled with the rod-receiving device.

Other pedicle screw systems such as U.S. Pat. Nos. 5,882,350 to Ralph et al.; 6,132,432 to Richelsoph; 4,950,269 to Gaines, Jr.; 6,626,908 to Cooper et al.; 6,402,752 to Schaffier-Wachter et al.; and 6,843,791 to Serhan may address some of the aforementioned drawbacks, but each of these pedicle screw systems are pre-operatively assembled, which makes these systems more difficult to install and maneuver in a spinal operation where MIS techniques are used.

BRIEF SUMMARY OF THE INVENTION

The invention is related to a bone fixation assembly, such as a pedicle screw system for the internal fixation of vertebral bodies. The pedicle screw system may be used for fixation of spinal segments and may be advantageous when minimally invasive surgery (MIS) techniques are employed. The pedicle screw system includes a tulip assembly comprising a tulip body, a inner member, and an expansion member. Installation of the pedicle screw system into pedicles of the spine, for example, includes inserting the pedicle screw into a portion of the spine and then coupling the tulip assembly to the pedicle screw. The tulip assembly may be locked onto the pedicle screw before a distraction rod is placed in the tulip assembly, after the distraction rod has been placed in the tulip assembly, but not yet locked therewith, or after the distraction rod has been placed in the tulip assembly and locked therewith. The tulip body and the inner member can be rotated relative to one another to lock the rod into the tulip assembly. In addition, the relative rotation may also provide additional locking of the tulip assembly to the pedicle screw.

In one aspect, a tulip assembly is coupled to a pedicle screw that has a threaded portion and a head portion. The tulip assembly includes a first device elastically expandable to receive the head portion of the pedicle screw; and a second device having a rod-receiving portion and an engagement portion, the engagement portion engageable with the first device to fix the tulip assembly to the head portion of the pedicle screw.

In another aspect, a pedicle screw system includes a pedicle screw having a threaded portion and a head portion; and a tulip assembly comprising a first device and a second device, the first device elastically expandable to receive the head portion of the pedicle screw, and the second device having a rod receiving portion and an engagement portion, the engagement portion engageable with the first device to fix the tulip assembly to the head portion of the pedicle screw.

In yet another aspect, a method of fixing a tulip assembly to a pedicle screw includes inserting the pedicle screw into bone, where the pedicle screw includes a head portion with a maximum diameter section; expanding a first device over and past the maximum diameter section of the pedicle screw after the pedicle screw is inserted into the bone; seating an inner surface of the first device against the head portion of the pedicle screw; and urging a portion of a second device into contact with a portion of the first device to fix the tulip assembly to the pedicle screw.

In still yet another aspect, a method of fixing a rod to a pedicle screw system, where the system includes a tulip assembly and a pedicle screw, includes inserting the pedicle screw into bone, the pedicle screw having a head portion that includes a maximum diameter section; coupling the tulip assembly to the pedicle screw by expanding a first device over and past the maximum diameter section of the pedicle screw, seating an inner surface of the first device against the head portion of the pedicle screw, and then urging a portion of a second device into contact with a portion of the first device to fix the tulip assembly to the pedicle screw; inserting a rod into the tulip assembly; and positioning a third device relative to the second device to fix at least a portion of the rod in the tulip assembly.

In still yet another aspect, a pedicle screw system includes a pedicle screw having a threaded portion and a spherical head portion; a poly-axial tulip assembly having a bore for accommodating the passage of the spherical head portion of the screw therethrough, the tulip assembly having an inner component, an outer component and a fastener assembly, the tulip assembly positioned on the head portion of the screw; wherein the fastener assembly is tapered along a top and a bottom edge, wherein an inner bore of the inner component is reciprocally tapered such that the fastener assembly mates with the inner component to allow the tulip assembly to be locked onto the head portion of the screw while allowing the tulip assembly to move poly-axially in relation to the screw; and wherein the outer component includes a retaining member along a top edge for receivably retaining the inner component in an engaged position, wherein the inner component lowered into a retained position locks an orientation of the tulip assembly relative to the screw.

In yet another aspect, a pedicle screw system includes a pedicle screw having a threaded portion and a spherical head portion; a poly-axial housing positioned on the head portion of the screw, the housing having an inner component, an outer component and a fastener assembly; wherein the fastener assembly is tapered along a top and a bottom edge and wherein an inner bore of the inner component is reciprocally tapered such that the fastener assembly mates with the inner component to allow the housing to be locked onto the head portion of the screw while allowing the housing to move poly-axially in relation to the screw; and wherein the fastener assembly includes pockets along an edge adjacent to the inner component, an edge of the inner component adjacent to the fastener assembly having reciprocal inclined planes for receivably retaining the inner component in an engaged position, wherein partially rotating the inner component provides a provisional rotational lock of the housing to the screw.

In another aspect, a pedicle screw includes a screw having threads and a head; a tulip coupled to the screw; a fastener internal to the tulip and positioned to couple the tulip to the screw; and an inner component of the tulip, the inner component of the tulip longitudinally moveable to engage the screw to provide a poly-axial lock between the tulip and the screw.

In yet another aspect, a method of connecting a rod to a pedicle screw system includes threading a screw having a head into bone of a patient; attaching a tulip assembly to the head of the screw; depressing a tulip inner component to lock the tulip to the screw; placing a rod into a channel of the tulip; and rotating the tulip inner component to capture the rod.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles ate not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. In addition, identical reference numbers identify similar elements or acts.

DETAILED DESCRIPTION OF THE INVENTION

By way of example, pedicle screw systems may be fixed in the spine in a posterior lumbar fusion process via minimally invasive surgery (MIS) techniques. The systems are inserted into the pedicles of the spine and then interconnected with rods to manipulate (e.g., correct the curvature, compress or expand, and/or structurally reinforce) at least portions of the spine. Using the MIS approach to spinal fixation and/or correction surgery has been shown to decrease a patient's recovery time and reduce the risks of follow-up surgeries.

The ability to efficiently perform spinal fixation and/or correction surgeries using MIS techniques is enhanced by the use of pedicle screw systems provided in accordance with the present invention, which systems provide many advantages over conventional systems. For example, a pedicle screw system in accordance with one embodiment provides the advantage that the pedicle screw may be inserted into the bone without being pre-operatively coupled with the rod-coupling assembly (hereinafter referred to as a tulip assembly). This is advantageous because the surgeon often needs to do other inter-body work after inserting the pedicle screw, but before attaching the larger and bulkier tulip assembly. Such an advantageous pedicle screw system may be even more crucial when using MIS techniques because the inter-body spatial boundaries in which the surgeon must work may be quite limited.

In addition, pedicle screw systems in accordance with the present invention advantageously allow a user to initially fix (e.g., lock) the tulip assembly to the pedicle screw at a desired angle before inserting and/or capturing the rod. Initially locking the tulip assembly to the pedicle screw means that at least one of the components of the tulip assembly is manipulated to grip and/or clamp onto the pedicle screw to reduce, if not prevent any translational and/or rotational movement of the tulip assembly relative to the pedicle screw. The ability to initially lock the tulip assembly to the pedicle screw may facilitate the surgeon in performing compression and/or distraction of various spinal and/or bone sections.

The term "distraction," when used in a medical sense, generally relates to joint surfaces and suggests that the joint surfaces move perpendicular to one another. However when "traction" and/or "distraction" is performed, for example on spinal sections, the spinal sections may move relative to one another through a combination of distraction and gliding, and/or other degrees of freedom.

Another advantageous feature of at least one embodiment of a pedicle screw system is to have an all-inclusive tulip assembly that can be coupled to the head portion of the pedicle screw intra-operatively. This advantageous tulip assembly may include the aspects or features that enable the tulip assembly to be initially locked onto the head portion of the pedicle screw and then to further receive, capture, and finally lock the rod into the tulip assembly. In one embodiment, the tulip assembly is initially locked onto the head portion of the pedicle screw after the rod has been received in the tulip assembly. This advantageous tulip assembly may decrease the complexity of the pedicle screw system installation by reducing the installation to essentially a three-step process, which is inserting the pedicle screw into bone, initially locking the tulip assembly onto the pedicle screw, which may be accomplished with or without the rod in the tulip assembly, and then capturing and locking the rod into the tulip assembly. In addition to accommodating the new MIS approach to spinal correction and/or fusion, at least one pedicle screw system described herein may include features to prevent, or at least reduce, the problems of cross-threading and/or post-operative tulip splaying, which is when the amount of stress/strain in rod, which may be caused by post-operative back flexion, forces open the tulip assembly and eventually leads to the disassembly and/or the failure of the pedicle screw system.

Pedicle Screw System

Figure 1:
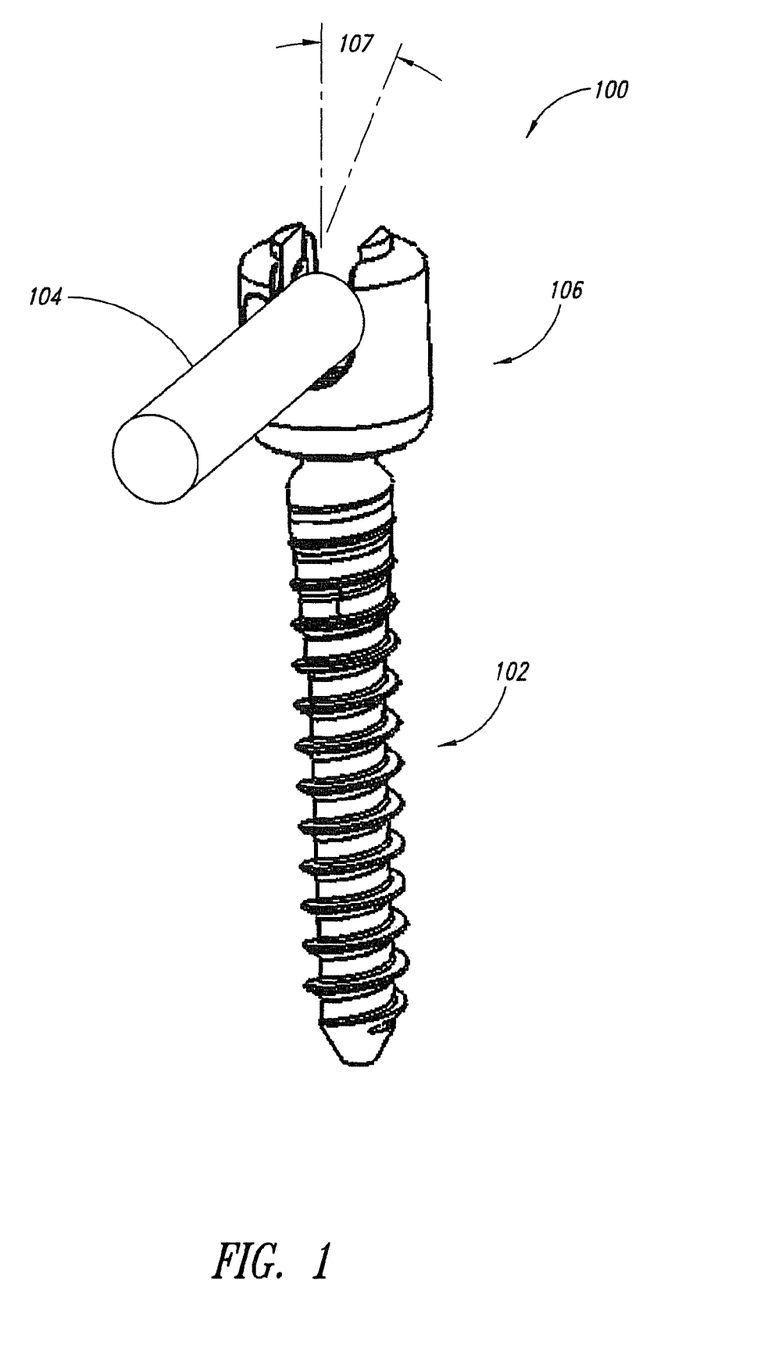
FIG. 1 is an isometric view of a pedicle screw system, according to one illustrated embodiment.

FIG. 1 generally shows a pedicle screw system 100 comprising a pedicle screw 102, a rod 104, and a coupling assembly 106, hereinafter referred to as a tulip assembly 106. The placement and/or number of pedicle screw systems 100 for a patient may be pre-operatively determined based on a pre-operative examination of the patient's spinal system using non-invasive imaging techniques known in the art, such as x-ray imaging, magnetic resonance imaging (MRI), and/or fluoroscopy imaging, for example. The tulip assembly 106 may be intra-operatively (i.e., during surgery) coupled to the pedicle screw 102 and maneuverable to achieve a desired placement, orientation, and/or angular position 20 of the tulip assembly 106 relative to the pedicle screw 102. Once the tulip assembly 106 is at the desired position relative to the pedicle screw 102, the tulip assembly 106 can be fixed or locked onto the pedicle screw 102. In one embodiment, the tulip assembly 106 is fixed onto the pedicle screw 102 before the rod is fixed or locked into the tulip assembly 106. In another embodiment, the tulip assembly 106 is fixed onto the pedicle screw 102 contemporaneously as the rod is fixed or locked into the tulip assembly 106.

It is understood that the relative, angular position 107 of a first tulip assembly 106 to a first pedicle screw 102 may be different from other pedicle screw systems 100 located elsewhere on a patient's spine. In general, the relative, angular position 107 of the tulip assembly 106 to the pedicle screw 102 allows the surgeon to selectively and independently orient and manipulate the tulip assemblies 106 of each pedicle screw system 100 installed into the patient to achieve and/or optimize the goals of the surgical procedure, which may involve compressing, expanding, distracting, rotating, reinforcing, and/or otherwise correcting an alignment of at least a portion of a patient's spine.

Figure 2:
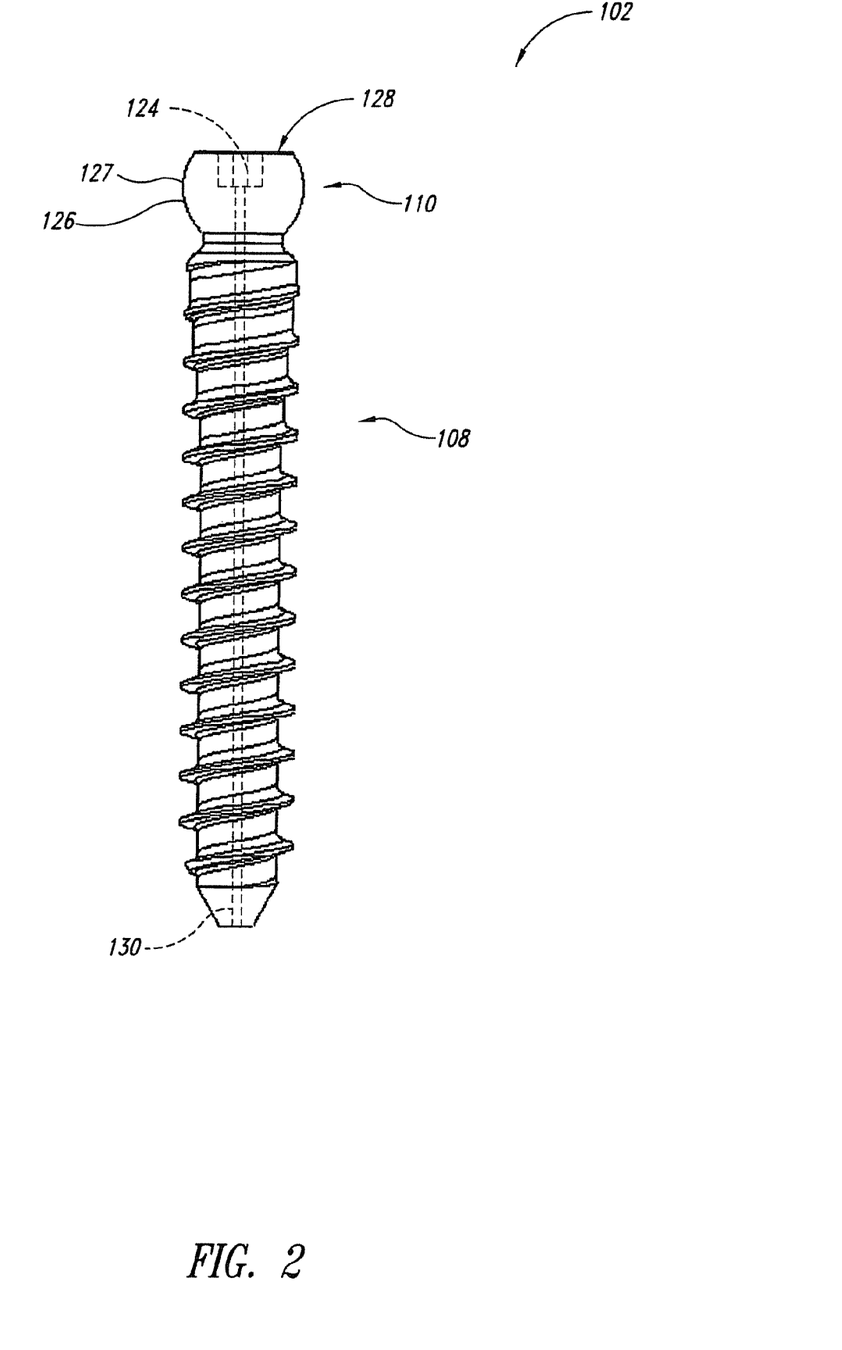
FIG. 2 is a side elevational view of a pedicle screw having a variable minor diameter, according to one illustrated embodiment.

FIG. 2 shows the pedicle screw 102 having an elongated, threaded portion 108 and a head portion 110. Although pedicle screws 102 are generally known in the art, the head portions 110 may be of varying configurations depending on what type of tulip assembly 106 is to be coupled to the pedicle screw 102. The head portion 110 of the pedicle screw 102 includes a driving feature 124 and a maximum diameter portion 126. The driving feature 124 permits the pedicle screw 102 to be inserted into a pedicle bone and/or other bone. The pedicle bone is a part of a vertebra that connects the lamina with a vertebral body. The driving feature 124 can be used to adjust the pedicle screw 102 even after the tulip assembly 106 is coupled to the pedicle screw 102. In the illustrated embodiment, the head portion 110 of the pedicle screw 102 is coupled to the threaded portion 108 and includes a generally spherical surface 127 with a truncated or flat top 20 surface 128.

In one embodiment, the pedicle screw 102 is cannulated, which means a channel 130 (shown in dashed lines and extending axially through the pedicle screw 102) extends through the entire length of the pedicle screw 102. The channel 130 allows the pedicle screw 102 to be maneuvered over and receive a Kirschner wire, commonly referred to as a K-wire. The K-wire is typically pre-positioned using imaging techniques, for example, fluoroscopy imaging.

Figure 3:
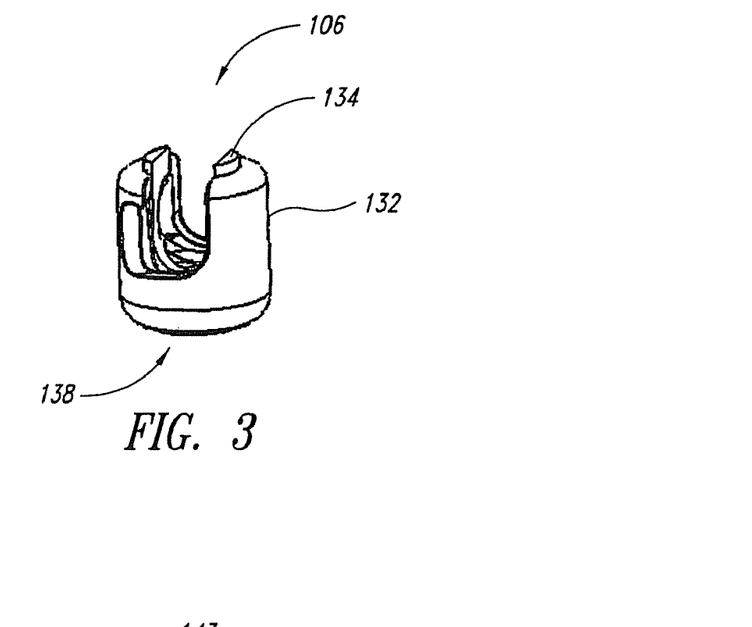
FIG. 3 is an isometric view of a tulip assembly of the pedicle screw system of FIG. 1.
Figure 4:
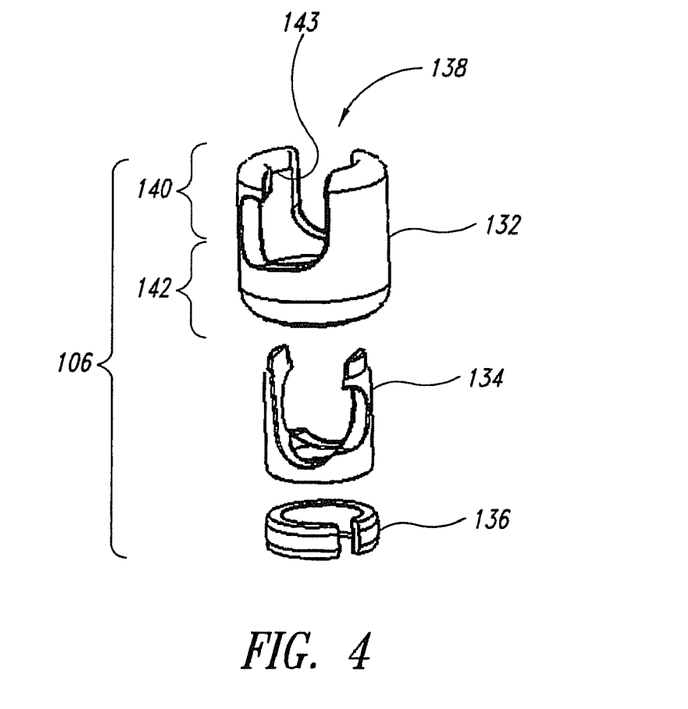
FIG. 4 is an isometric, exploded view of the tulip assembly of FIG. 3.

FIGS. 3 and 4 show the tulip assembly 106 that includes a first member or tulip body 132, an inner member or inner member 134, and an expansion/contraction member or split ring 136, according to one illustrated embodiment. The tulip body 132 includes a bore or central bore 138, an upper portion 140, a lower portion 142, and an internal lip 143. In one embodiment, the tulip body 132, the inner member 134, and the split ring 136 are pre-operatively assembled before being placed onto the head portion 110 of the pedicle screw 102. Both the inner member 134 and the split ring 136 may be inserted into the tulip body 132 through the bore 138 upward or through the lower portion 142 of the tulip body 132.

Figure 5:
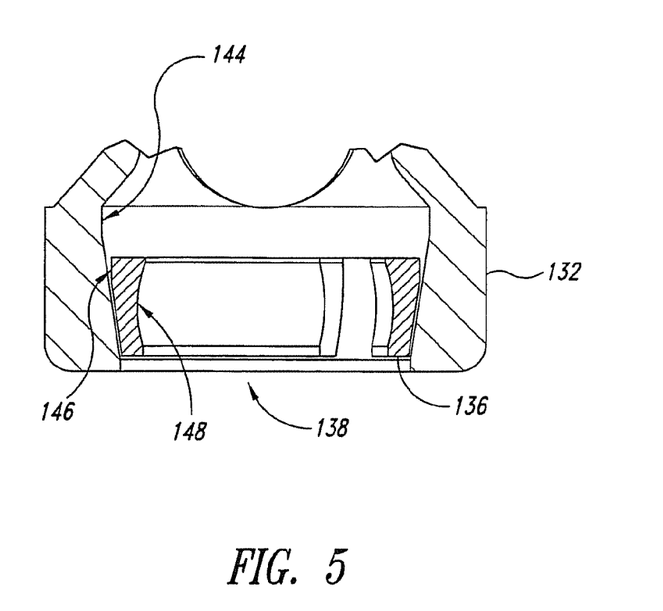
FIG. 5 is partial, cross-sectional view of a split ring and tulip body of the tulip assembly of FIG. 3.

FIG. 5 shows the split ring 136 inserted in the lower portion 142 of the tulip body 132. For purposes of clarity, the upper portion 140 of the tulip body, the pedicle screw 102, and the inner member 134 are not shown. An inner surface 144 of the bore 138 through the lower portion 142 of the tulip body 132 is sized to allow the split ring 136 to float and/or translate upwards so that the split ring 136 can expand to receive the head portion 110 of the pedicle screw 102. The split ring 136 includes an outer surface 146 and an inner surface 148. The outer surface 146 of the split ring 136 frictionally contacts the inner surface 144 of the bore 138 of the tulip body 132. The inner surface 148 of the split ring 136 frictionally engages the head portion 110 of the pedicle screw 102, as will be described in more detail below. In one embodiment, the split ring 136 is fabricated to be elastically expandable and contractible within the range of operations described herein.

Figure 6:
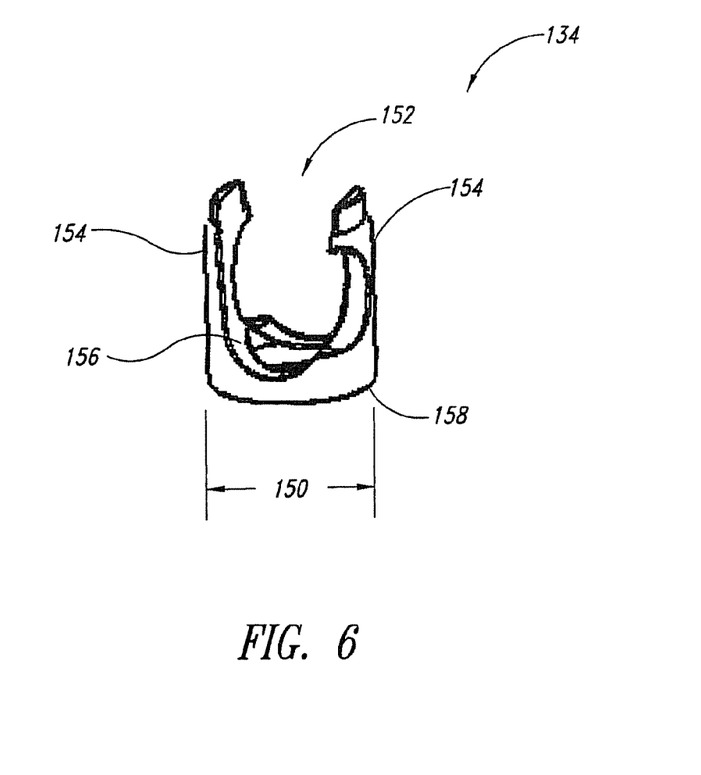
FIG. 6 is an isometric view of a inner member of the tulip assembly of FIG. 3.

FIG. 6 shows the inner member 134 having an outer diameter 150, a contoured channel 152 formed by extending arms 154, which includes a rod-support surface 156, and a bottom surface 158. The outer inner diameter 150 is sized to be received in the bore 138 of the tulip body 132 and then be rotatable within the tulip body 132, as will be described in more detail below. The contoured channel 152, along with the rod-support surface 156, operates in cooperation with the tulip body 132 to receive, capture, and eventually lock the rod 104 into the tulip assembly. The bottom surface 158 operates to engage the split ring 136 and force the split ring 136 down in the bore 138 of the tulip body 132, which results in contraction of the split ring 136 around the head portion 110 of the pedicle screw 102. It is understood that the forced contraction of the split ring 136 along with the radial constraint provided by the inner surface 144 of the tulip body 132 generates sufficient radial pressure on the head portion 110 of the pedicle screw 102 to lock the tulip body 132 onto the pedicle screw 102

Pedicle Screw System Installation

Figures 7A, 7B, 7C:
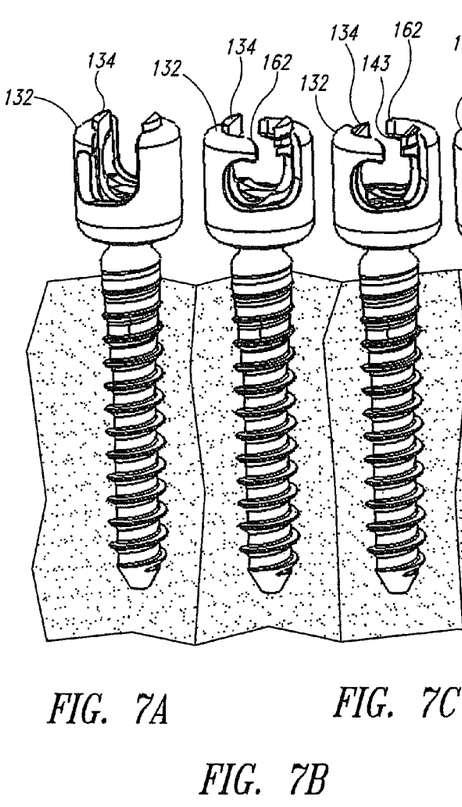
FIGS. 7A-7D are isometric views of a method of installing a pedicle screw system into bone, according to the illustrated embodiments.

FIGS. 7A-7C show various stages of assembly and/or installation of the tulip assembly 106 to the pedicle screw 102. In the illustrated embodiments, the pedicle screw 102 has already been inserted into bone material 160. In FIG. 7A, the tulip assembly 106 is snapped onto the head portion 110 of the pedicle screw 102. The inner surface 148 of the split ring 136 mates with the head portion 110 of the pedicle screw 102. As the tulip assembly 106 is pushed onto the head portion 110 of the pedicle screw 102, the split ring 136 expands and snaps onto the head portion 110. The split ring 136 is initially pushed up into the bore 138 of the tulip body 132, as described above. The bore 138 in the lower portion 142 of the tulip body 132 permits the split ring 136 to float in the bore 138. Alternatively stated, as the split ring 136 is pushed upwards inside of the tulip body 132 by the head portion 110 of the pedicle screw, sufficient clearance is present for the split ring 136 to expand and snap around the head portion 110 of the screw 102. At this point, the tulip assembly 106 is rotationally coupled to the head portion 110 of the pedicle screw 102. The tulip assembly 106 may be rotated to achieve a desired orientation with respect to the pedicle screw 102 and the initial coupling mechanisms just described reduce the likelihood that the tulip assembly 106 will be detached from the pedicle screw 102 during manipulation thereof.

Next, the mating tapered surfaces, which comprise the head portion 110 of the pedicle screw 102, the outer and inner surfaces 146, 148 of the split ring 136, and the inner surface 144 of the lower portion of the bore 138 of the tulip body 132, cooperate to lock the tulip assembly 106 onto the head portion 110 01: the pedicle screw. An upward force applied to the tulip body 132 tends to cause further compression and/or contraction of the split ring 136 because the split ring 136 is forced down further along the inner surface 144 of the bore 138 of the tulip body 132. Such additional compression and/or contraction of the split ring 136 substantially locks or fixes the tulip assembly 106 onto the pedicle screw 102, thus preventing additionally rotation, manipulation, loosening, and/or removal of the tulip assembly 106 with respect to the pedicle screw 102. In short, when the tulip assembly 106 is initially placed onto the head portion 110 of the pedicle screw 102, the tulip assembly 106 is free to move poly-axially in relation to the pedicle screw 102. Thus, the tulip assembly 106 remains free to rotate on the pedicle screw 102 until it is locked onto the head portion 110 of the pedicle screw 102, where the locking will be described below. In addition, both the tulip body 132 and the inner member 134 are aligned to receive the rod 104. For purposes of clarity, however, the rod 104 is not shown so that the features of the tulip assembly 106 that capture and lock the rod 104 are more readily viewable.

FIG. 7B shows that the tulip body 132 and the inner member 134 are rotated, about a common axis, to begin capturing the rod 104. In one embodiment, the inner member 134 is held while the tulip body 132 is rotated. In another embodiment, the tulip body 132 is held while the inner member 134 is rotated. In yet another embodiment, the inner member 134 and the tulip body 132 are rotated relative to one another, with both components being rotated at the same time. The tulip body 132 includes extensions 162 that cooperate with the contoured channel 152 and arms 154 of the inner member 134 to begin the capture of the rod 104.

In addition, the inner member 134 may be rotated clockwise to retain the rod 104 and/or the tulip body 132 rotated counterclockwise. Alternatively the inner member 134 may be rotated counterclockwise and/or the tulip body 132 may be rotated clockwise. The rod 104 is initially retained on the contoured surface 156 of the inner member 134, which includes a rod-capturing portion 164 (best shown in FIG. 7D). The inner member 134 cooperates with the bore 138 of the tulip body 132 to capture the rod 104. In addition, the inner member 134, after being rotated relative to the tulip body 132 to capture the rod 104, provides structural reinforcement to the tulip body 132 to prevent the tulip body 132 from splaying open under post-operative dynamic and static loading, for example.

As shown in FIGS. 7A and 7B, the arms 154 of the inner member 134 are flexed inwards and protrude above the top surface of the tulip body 132. In FIG. 7C, the inner member 134 is forced or pushed down into the tulip body 132 so that the top portion of the inner member 134 is approximately flush with the top portion of the tulip body 132. An additional or continued downward force on the inner member 134 causes the inner member 134 to snap or engage under the lip 143 located in the upper portion 140 of the tulip body 132. Hence, the elasticity of the arms 154 of the inner member 134 permit the arms to flex inward when pushed down and then expand to become engaged under the lip 143 of the tulip body 132. This longitudinal engagement to retain the inner member 134 within the tulip body 132 may be accomplished either before or after the rod 104 is placed in the tulip assembly 106. In one embodiment, forcing the inner member 134 down into the tulip body 132 may provide additional locking capacity of the tulip assembly 106 onto the pedicle screw 102 because the bottom surface 158 of the inner member 134 pushes the split ring 136 even further down along the inner surface 144 of the bore 138 of the tulip body 132. As described above, this action clamps the tulip assembly 132 onto the head portion 110 of the pedicle screw.

In an alternate embodiment, forcing the inner member 134 down into the tulip body 132 may provide the initial locking of the tulip assembly 106 onto the pedicle screw 102. Depending on the configuration of the relative, interacting surfaces, and possibly other factors, the process of forcing the inner member 134 downward to be retained in tulip body 132 may, according to one embodiment, establish the initial lock of the tulip, assembly 106 to the pedicle screw 102.

Figure 7D:
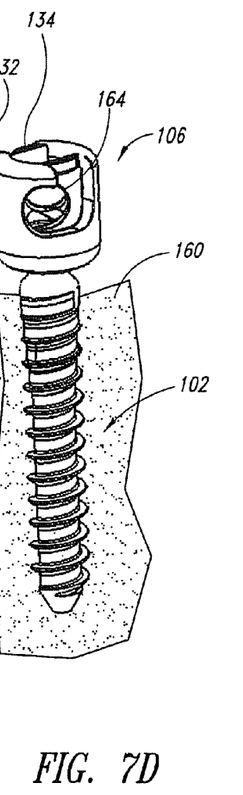

FIG. 7D shows the tulip assembly 106 in a locked or closed position where the rod 104 is locked into the tulip assembly 106. As shown in the illustrated embodiment, a slight overlap occurs between the extensions 162 of the tulip body 132 and the arms 154 of the inner member 134. The additional amount of relative rotation illustrated from FIGS. 7C to 7D completes the rod-locking process to securely lock the rod 104 in the tulip assembly 106, according to the illustrated embodiment.

FIGS. 8 through 11 show alternative embodiments of pedicle screw systems. These alternative embodiments, and other alternatives described herein, are substantially similar to previously described embodiments. Structural aspects and/or features and assembly/installation steps that are common to the previously described embodiments are identified by like reference numbers. Only significant differences in operation and structure are described below.

Figure 8:
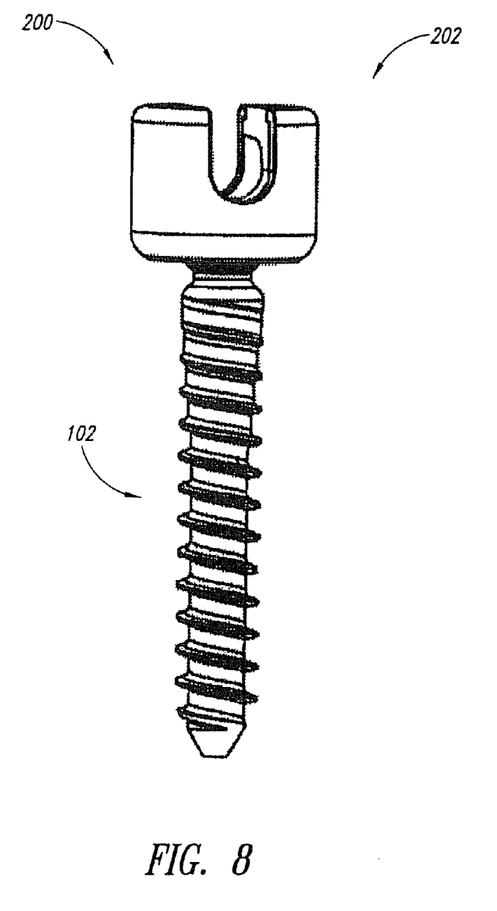
FIG. 8 is a side elevational view of a pedicle screw system, according to another illustrated embodiment.
Figure 9:
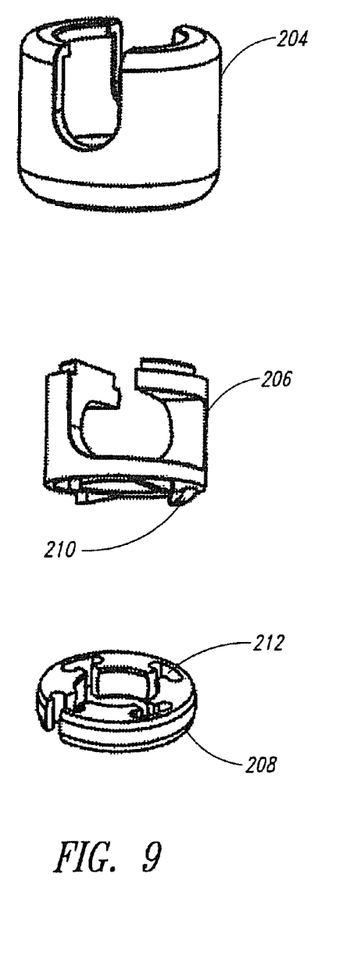
FIG. 9 is an isometric, exploded view of a tulip assembly of the pedicle screw system FIG. 8.
Figure 10:
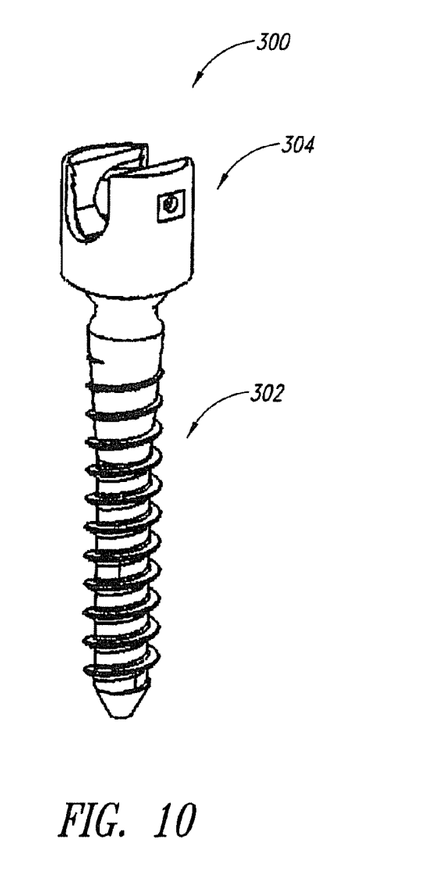
FIG. 10 is a side elevational view of a pedicle screw system, according to another illustrated embodiment.
Figure 11:
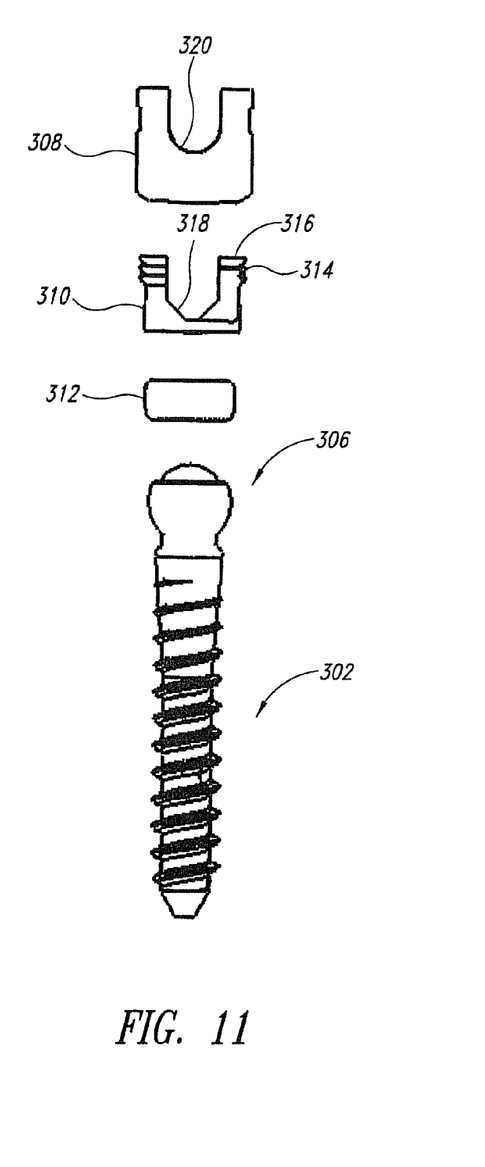
FIG. 11 is an isometric, exploded view of a tulip assembly and a pedicle screw of the pedicle screw system FIG. 10.

FIGS. 8 and 9 show an alternative embodiment of a pedicle screw system 200, according to the illustrated embodiment. The pedicle screw system 200 includes the pedicle screw 102 with an alternative tulip assembly 202. The tulip assembly 202 comprises a tulip body 204, a inner member 206, and an expansion member or split ring 208. In the illustrated embodiment, the inner member 206 includes inclined planes 210 to provide a different method and structure for initially locking the angle of the tulip assembly 202 to the pedicle screw 102. The initial locking is achieved by rotating the inner member 206 partially through its allowable rotation. The inclined planes 210 of the inner member 206 engage with pockets 212 present in the expansion member 208. The inclined planes 210 operate as cam extensions on the inner member 206 to force the expansion member 208 downward and into a tight compression, thus locking the tulip assembly 202 onto the head portion 110 of the pedicle screw 102 FIGS. 10 and 11 show a pedicle screw system 300 in accordance with yet another embodiment. FIG. 11 is an exploded view of the pedicle screw system 300 of FIG. 10. The pedicle screw system 300 includes a pedicle screw 302 and a tulip assembly 304. The pedicle screw 302 includes a dual diameter head portion 306. The tulip assembly 304 includes a tulip body 308, an inner member 310, and an expansion member or split ring 312.

According to aspects of the illustrated embodiment, the rod (not shown) is captured and then subsequently locked by rotating the inner member 310. An initial lock is achieved between the tulip assembly 304 and the pedicle screw 302 by pushing the inner member 310 down into the tulip body 308. Barbed surfaces 314 on the inner member 310 engage barbed surfaces in the tulip body 308 to retain the inner member 310 inside the tulip body 308. The inner member 310, in turn, pushes on the split ring 312 to lock the tulip assembly 304 onto the pedicle screw 302. In addition, inclined planes (not shown) may be located on the arms 316 of the inner member 310 to force the rod tightly against a first rod slot 318 in the inner member 310 and/or in a second rod slot or rod capture channel 320 in the tulip body 308. Thus, the rotation of the inner member 310 relative to the tulip body 308 locks the rod in the tulip assembly 304.

In operation, the pedicle screw systems as described, but not limited to the embodiments herein, are designed for fixation of bone material and/or bone segments during a surgical procedure, such as fusing spinal segments in which MIS techniques are employed. For example, the pedicle screw system is inserted into the pedicles of the spine and then interconnected with rods to provide support to the spine to allow for post-operative fusion of the spinal segments. While the pedicle screw can be inserted with the tulip assembly coupled with the pedicle screw, one embodiment for the installation of the pedicle screw system includes inserting the pedicle screw into the bone and subsequently coupling the tulip assembly to the pedicle screw, where such an approach has advantages over currently known pedicle screw system assemblies and/or installations.

In addition, various structural features of the pedicle screw systems as described, but not limited to the embodiments herein, may provide other advantages over existing pedicle screw systems. First, the pedicle screw may be inserted into the bone without the presence of the tulip assembly or rod, which permits the surgeon to place the screw and then perform subsequent inter-body work without having to work around the tulip assembly or the rod. Second, the tulip assembly includes a mechanism for capturing the rod that eliminates problems associated with conventional pedicle screws, such as cross-threading, because the pedicle screw systems disclosed herein do not use any threads to couple the tulip assembly to the pedicle screw or to capture and lock the rod into the tulip assembly. Third, the interface between the head portion of the pedicle screw and the tulip assembly provides an initial lock, which allows the angle of the tulip assembly to be set or fixed with respect to the pedicle screw before insertion of the rod and/or before the rod is captured in the tulip assembly. With this type of pedicle screw system, the surgeon has the ability to check and even double check the placement, angle, and/or orientation regarding aspects of the pedicle screw system to facilitate, and even optimize, the compression, distraction, and/or other manipulation of the spinal segments. Further, the pedicle screw systems accommodate the new MIS techniques being applied to spinal operations.

One possible post-operative advantage of the pedicle screw systems is that the cooperation and interaction of the inner member with the tulip body of the tulip assembly substantially reduces and most likely prevents the known problem of tulip splaying. Tulip splaying is generally regarded as a post-operative problem of when a stressed rod forces open portions of the tulip body, which eventually leads to the disassembly and likely failure of the pedicle screw system within the patient. Yet another post-operative advantage of the pedicle screw systems is that unlike existing rod-coupling members or constructs, the tulip assemblies described herein have a smaller size envelope (e.g., less bulky, lower profile, and/or more compact shape) and are easier to place onto the pedicle screw. The smaller size and ease of installation may reduce trauma to the soft-tissue regions in the vicinity of the surgical site, which in turn generally allows for a quicker recovery by the patient. Yet another possible advantage of the pedicle screw systems over existing systems is that all of the parts needed to lock the tulip assembly to the pedicle screw and to capture and lock the rod into the tulip assembly are included within the tulip assembly. Accordingly, once the tulip assembly is snapped or otherwise coupled to the pedicle screw, no additional locking cap or threaded fastener is needed to complete the assembly/installation of the pedicle screw system. According to aspects described herein, and as appended by the claims, the inventive pedicle screw systems permit inserting the pedicle screw without the tulip assembly coupled thereto, locking the tulip assembly onto the pedicle screw, and subsequently capturing and locking the rod into the tulip assembly.

The various embodiments described above can be combined to provide further embodiments. All of the above U.S. patents, patent applications, provisional patent applications and publications referred to in this specification, to include, but not limited to U.S. Provisional Patent Application Nos. 60/622,107 filed Oct. 25, 2004; 60/622,180 filed Oct. 25, 2004; 60/629,785 filed Nov. 19, 2004; 60/663,092 filed Mar. 18, 2005; and 60/684,697 filed May 25, 2005 are incorporated herein by reference in their entirety. Aspects of the invention can be modified, if necessary, to employ various systems, devices and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all bone fixation systems and methods that operate in accordance with the claims. Accordingly, the invention is not limited by the disclosure, but instead its scope is to be determined entirely by the following claims.

What I claimed is:

1. A bone fixation assembly for fixation of vertebral bodies, said bone fixation assembly comprising:
    a pedicle screw having a head and a threaded portion; and
    a tulip body configured to receive said pedicle screw and a rod, said tulip body comprising a tapered wall that defines at least a portion of a central bore extending along an axis of said tulip body;
    said tulip body also having a rod capture channel opening through an end of said tulip body and in communication with said central bore;
    said rod capture channel having a rod reception portion and a rod securing portion, said rod securing portion of said rod capture channel being defined by two opposing surfaces extending at least partially about said axis of said tulip body so that said rod can pass between said two opposing surfaces and be received in said rod securing portion of said rod capture channel;
    an expansion member received on said head for locking said tulip body onto said head, said expansion member received on said head and compressing on said head in response to longitudinal relative movement of said expansion member along said tapered wall;
    wherein said tulip body is configured to be free to move polyaxially on said head of the pedicle screw after said pedicle screw is screwed into bone and prior to said compression;
    said rod reception portion of said rod capture channel receiving said rod and when there is rotation of said tulip body, said rod becomes captured and locked in said rod securing portion of said rod capture channel;
    said locking of said expansion member on said head being separate from and prior to said locking of said rod in said tulip body when said bone fixation assembly as fixed to at least one of the vertebral bodies.

2. The bone fixation assembly of claim 1, wherein said tulip body comprises:
    an outer body defining said central bore; and
    a plurality of extension members disposed on said outer body, said plurality of extension members defining said rod capture channel.

3. The bone fixation assembly of claim 2, wherein said tulip body further comprises:
    a top portion and a bottom portion;
    wherein said rod capture channel is defined in said top portion of said tulip body.

4. The bone fixation assembly of claim 3, wherein said expansion member further comprises a head reception member disposed in said bottom portion of said tulip body;
    wherein said head reception member is configured to expandably receive said head of said pedicle screw;
    and wherein said bottom portion of said tulip body includes said tapered wall, which is configured to selectively compress said on head reception member to retain said head portion of said pedicle screw.

5. The bone fixation assembly of claim 4, wherein said head reception member comprises a split ring.

6. The bone fixation assembly of claim 5, further comprising an inner member;
    wherein said inner member is sized to be disposed in said tulip body.

7. The bone fixation assembly of claim 2, wherein said plurality of extension members mirrors an outer profile of said tulip body.

8. The bone fixation assembly of claim 7, wherein said; rod securing portion is transverse to said rod reception portion.

9. A bone fixation assembly comprising:
    a tulip assembly, said tulip assembly comprising:
    a pedicle screw having a head and a threaded portion;
    a tulip body configured to receive a rod, said tulip body including an outer body, said outer body comprising a tapered wall that defines at least a portion of a central bore extending along an axis of said tulip body, and a plurality of extension members disposed on said outer body, said plurality of extension members defining a rod capture channel;
    wherein said rod capture channel defined by said plurality of extension members includes a rod reception portion and a rod securing portion, said rod securing portion being in communication with said rod reception portion and transverse to said rod reception portion; said rod securing portion of said rod capture channel being defined by two opposing surfaces extending at least partially about said axis of said tulip body so that said rod can pass between said two opposing surfaces and be received in said rod securing portion of said rod capture channel; and
    wherein said rod capture channel opens through an end of said tulip body and in communication with said central bore
    an expansion member received on said head for locking said tulip body onto said head, said expansion member received on said head and compressing said head in response to longitudinal relative movement of said expansion member along said tapered wall;
    said rod reception portion of said rod capture channel receiving said rod and when there is rotation of said tulip body, said rod becomes captured and locked in said rod securing portion of said rod capture channel;
    said locking of said expansion member on said head being separate from and prior to said locking of said rod in said tulip body when said bone fixation assembly as fixed to at least one of the vertebral bodies.

10. The bone fixation assembly of claim 9, wherein said plurality of extension members mirrors an outer profile of said tulip body.

11. The bone fixation assembly of claim 9, wherein said tulip body further comprises:
    a top portion and a bottom portion;
    wherein said rod capture channel is defined in said top portion of said tulip body.

12. The bone fixation assembly of claim 3, wherein said expansion member further comprises a head reception member disposed in said bottom portion of said tulip body;

wherein said head reception member is configured to expandably receive said head of said pedicle screw;

and wherein said bottom portion of said tulip body includes said tapered wall, which is configured to selectively compress said head reception member to retain said head portion of said pedicle screw.

* * * * *

UNITED STATES PATENT AND TRADEMARK OFFICE
CERTIFICATE OF CORRECTION

| | | |
|---|---|---|
| PATENT NO. | : 8,092,504 B2 | Page 1 of 1 |
| APPLICATION NO. | : 11/942443 | |
| DATED | : January 10, 2012 | |
| INVENTOR(S) | : David R. Warnick | |

It is certified that error appears in the above-identified patent and that said Letters Patent is hereby corrected as shown below:

In the Specification

In Column 9, Line 37, after 102, please insert -- . --.

In the Claims

In Column 12, Line 6, Claim 4, after compress, please delete "said on" and insert -- on said -- therefor.

In Column 12, Line 17, Claim 8, after said, please delete ";".

Signed and Sealed this
Eleventh Day of February, 2014

Michelle K. Lee
*Deputy Director of the United States Patent and Trademark Office*

UNITED STATES PATENT AND TRADEMARK OFFICE
CERTIFICATE OF CORRECTION

Page 1 of 2

PATENT NO. : 8,092,504 B2
APPLICATION NO. : 11/942443
DATED : January 10, 2012
INVENTOR(S) : David R. Warnick It is certified that error appears in the above-identified patent and that said Letters Patent is hereby corrected as shown below:

On the Title Page, in item (57), first paragraph, line 5, before inner, please delete "a" and insert --an-- therefor.

In the Specification

In Column 1, Line 65, please delete "2005/019:2573", and insert --2005/0192573-- therefor.

In Column 2, Line 35, please delete "Schaffier-Wachter et al." and insert --Schaffler-Wachter et al.-- therefor In Column 2, Line 50, before inner, please delete "a" and insert --an-- therefor.

In Column 3, Line 9, please delete "rod receiving" and insert --rod-receiving-- therefor.

In Column 4, Line 24, please delete "ate" and insert --are-- therefor.

In Column 4, Line 43, before inner, please delete "a" and insert --an-- therefor.

In Column 4, Line 51, before FIG. 8, please insert --in--.

In Column 4, Line 55, before FIG. 10, please insert --in--.

In Column 6, Line 7, please delete "20".

In Column 6, Line 44, please delete "20".

This certificate supersedes the Certificate of Correction issued February 11, 2014.

Signed and Sealed this
Twenty-second Day of July, 2014

Michelle K. Lee
*Deputy Director of the United States Patent and Trademark Office*

CERTIFICATE OF CORRECTION (continued)
U.S. Pat. No. 8,092,504 B2

In Column 7, Line 63, please delete "01:" and insert --of-- therefor.

In Column 8, Line 62, please delete "132" and insert --106-- therefor

In Column 9, Line 25, before inner, please delete "a" and insert --an-- therefor.

In Column 9, Line 37, after 102, please insert --.--.

In the Claims

In Column 12, Line 6, Claim 4, after compress, please delete "said on" and insert --on said-- therefor.

In Column 12, Line 17, Claim 8, after said, please delete ";".